US00PP10587P

United States Patent [19]

Elsner

[11] Patent Number: Plant 10,587

[45] Date of Patent: Sep. 1, 1998

[54] VARIETY OF GERANIUM NAMED 'VALENTINE'

[75] Inventor: Wilhelm Elsner, Dresden, Germany

[73] Assignee: Elsner Pac Jungpflanzen, Germany

[21] Appl. No.: 746,424

[22] Filed: Nov. 8, 1996

[51] Int. Cl.[6] ..... A01H 5/00

[52] U.S. Cl. ..... Plt./87.12

[58] Field of Search ..... Plt./87.12

*Primary Examiner*—James R. Feyrer
*Assistant Examiner*—Melissa L. Kimball
*Attorney, Agent, or Firm*—Webb Ziesenheim Bruening Logsdon Orkin & Hanson, P.C.

[57] ABSTRACT

The new cultivar is an early, rich flowering variety. Its elegant deep pink flowers with a very distinct magenta eye is very attractive over the medium green foliage. The cultivar produces big umbels and continuously flower. It demonstrates good garden and greenhouse performance. The new cultivar is an improvement in comparison to the current varieties "First Kiss" and "L'amour."

1 Drawing Sheet

BACKGROUND OF THE INVENTION

The present invention comprises a new and distinct cultivar of *Pelargonium×hortorum* known in the United States by the varietal name 'Valentine' (and marketed in the United States as 'PAC Valentine (Jonos)' and known in Europe by the varietal name 'Jonos'). The new cultivar was discovered at Elsner pac Jungpflanzen in Dresden, Germany in 1995. The new variety was discovered in a cultivated area and is a mutation of the unpatented variety 'Jana'. The new variety was first asexually reproduced by cuttings at Elsner pac Jungpflanzen in Dresden, Germany in 1995. It has also been trial and field tested in Dresden, Germany and at Oglevee Ltd. in Connellsville, Pa. and has been found to retain its distinctive characteristics through successive propagations.

The plant history was taken on six week plants blossomed under the natural light in a greenhouse in 10 cm pots. The culivar when grown in a glass greenhouse was potted on Feb. 13, 1996 and flowered on Mar. 25, 1996.

DESCRIPTION OF THE DRAWING

The accompanying photographic drawing illustrates the new cultivar, the color being as nearly true as possible with color illustrations of this type.

DESCRIPTION OF THE NEW PLANT

The following detailed description sets forth the characteristics of the new cultivar. The data which defines these characteristics were collected from asexual reproductions carried out by Oglevee, Ltd. in Connellsville, Pa. The plant history was taken on six week plants blossomed under natural light in a greenhouse and the color readings were taken indoors under 200–220 footcandles of cool white fluorescent light. Color references are primarily to The R.H.S. Colour Chart of The Royal Horticultural Society of London.

The Plant

Classification:

*Botanical.*—*Pelargonium×hortorum.*
*Commercial.*—Florists' zonal geranium.
*Form.*—Medium mound, uniform.
*Height.*—15.0–17.5 cm.
*Growth.*—Free basal branching.

*Strength.*—Stands upright without artificial support.
*Foliage.*—Stalked leaf attachment.

Leaves:

*Size.*—7.5–9.0 cm.
*Shape.*—Reniform.
*Margin.*—Crenate.
*Texture.*—Pubescent, slightly reflective, smooth.
*Color.*—Top: Green Group 137A. Bottom: Green Group 138A. Zone: No prominent zone present.
*Ribs and veins.*—Venation: Palmate. Color: Yellow-Green Group 144C.

Petioles:

*Color.*—Yellow-Green Group 144A.
*Length.*—6.0–11.0 cm.

Stem:

*Color.*—Yellow-Green Group 144B.
*Internodes.*—2.0–3.0 cm in length.

The Bud (Umbel)

Shape: Upright hemispherical clusters.
Size: 3.0 cm, just cracking color.

Inflorescence

Blooming habit: Free and early flowering, semi-double, continuous.
Size (diameter): 4.5–7.5 cm, fully open bloom.
Borne: Umbel, floret on pedicel, pedicel on peduncle, flowers 7.5–10.0 cm above the foliage.

Florets:

*Closed size.*—1.0–1.5 cm, just cracking color.
*Form.*—Slightly cupped, ruffled.
*Color.*—Top: Red-Purple Group 67B. Bottom: Red-Purple Group 67C at outer edge fading to Red-Purple Group 68D with veins of Red-Purple Group 68A. Eye: Bottom 4–7 petals: Red-Purple Group 66A "spot" with white at very middle. Top petals: Red-Purple Group 66A with white at center.

Petals:

*Quantity.*—6–9.
*Size.*—2.5–3.0 cm.
*Texture and appearance.*—Smooth, reflective.

Petaloids:

*Quantity.*—1–2.
*Shape.*—Irregular, twisted, ruffled.

*Color.*—Top: Red-Purple Group 67C, some having a Red-Purple Group 66A eye. Bottom: Red-Purple Group 68D.

Pedicel:

*Color.*—Red-Purple Group 60A with Yellow-Green Group 144A.

*Length.*—2.5–4.0 cm.

Peduncle:

*Color.*—Yellow-Green Group 144A.

*Length.*—16.5–22.0 cm.

Disease resistance: Not known.

Reproductive Organs

Stamens:

*Anthers.*—3.0 mm in length.

*Filaments.*—Length: 9.0–10.0 mm. Color: White.

*Pollen.*—Golden Orange.

Pistils:

*Number.*—5–6.

*Length.*—1.0 mm.

*Stigma.*—Color: Deep Magenta/Purple.

*Style.*—Length: 4.0 mm.

*Ovaries.*—Length: 7.0 mm. Color: Pale Green. Characteristics: Superior.

Fruit: None observed.

General Characteristics

1. New deep pink color with a very distinct magenta eye.

2. Early, free flowering.

3. Elegant flowers, big umbels and continuous flowering.

4. Similar in appearance to with certain morphological differences from the current varieties 'First Kiss' (PPO9168) and 'L'amour' (U.S. Plant Pat. No. 9,287) but having greatly improved heat tolerance, greenhouse performance and outdoor garden performance over 'First Kiss' and 'L'amour'.

I claim:

1. A new and distinct variety of geranium plant substantially shown and described.

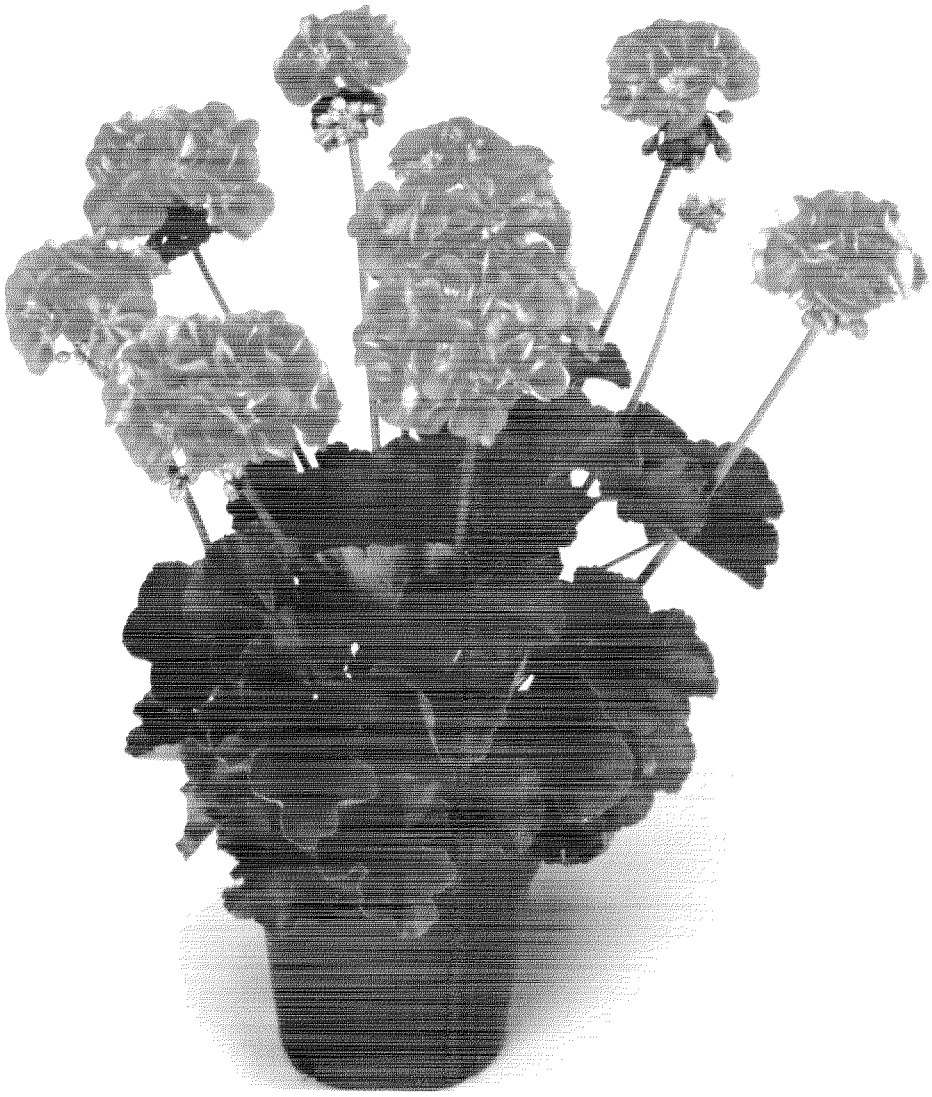

* * * * *